United States Patent [19]
Burky et al.

[11] Patent Number: 6,119,574
[45] Date of Patent: Sep. 19, 2000

[54] BLAST EFFECTS SUPPRESSION SYSTEM

[75] Inventors: Thomas E. Burky, Fredricktown; Donald J. Butz, Columbus; John S. Butz, Caledonia, all of Ohio; Scott M. Golly, Baldwin, Md.; Graham H. Alexander, Blacklick, Ohio

[73] Assignee: Battelle Memorial Institute, Columbus, Ohio

[21] Appl. No.: 09/109,966

[22] Filed: Jul. 2, 1998

[51] Int. Cl.⁷ ............................................. F41H 5/24
[52] U.S. Cl. .................. 89/36.04; 102/303; 89/1.11; 86/50
[58] Field of Search ................ 89/1.1, 1.11, 36.01, 89/36.02, 36.04; 86/50

[56] References Cited

U.S. PATENT DOCUMENTS

| | | | |
|---|---|---|---|
| 4,372,395 | 2/1983 | Hammett . | |
| 4,543,872 | 10/1985 | Graham et al. . | |
| 4,589,341 | 5/1986 | Clark et al. . | |
| 4,597,451 | 7/1986 | Moore et al. . | |
| 4,836,079 | 6/1989 | Barrett | 86/50 |
| 4,903,573 | 2/1990 | Browne et al. | 86/50 |
| 4,964,329 | 10/1990 | Moxon et al. | 86/50 |
| 5,119,877 | 6/1992 | Sapko et al. . | |
| 5,134,921 | 8/1992 | Breed et al. | 86/50 |
| 5,154,237 | 10/1992 | Cooper . | |
| 5,172,767 | 12/1992 | Turner et al. . | |
| 5,224,550 | 7/1993 | Bragg . | |
| 5,249,500 | 10/1993 | Husseiny et al. | 89/1.11 |
| 5,728,967 | 3/1998 | Parkes | 102/303 |

OTHER PUBLICATIONS

LBA Systems, Ltd., United Kingdom, "LBA Systems Bomb Inhibitor" pp. 1–6, dated 1994/95.

General Plastics Manufacturing Company, U.S.A., Preliminary Product Data Sheet "Blast–A–Foam", pp. 1–6 dated Apr. 9, 1998.

W.A.Keenan and P.C. Wager, U.S.A., "Motigation of Confined Explosion Effects by Placing Water in Proximity of Explosives", pp. 311–339, dated Aug. 1992.

*Primary Examiner*—Charles T. Jordan
*Assistant Examiner*—M Thomson
*Attorney, Agent, or Firm*—Kremblas, Foster, Millard & Pollick

[57] ABSTRACT

A blast suppression system is provided, with the system including a plurality of command-actuated units located in the immediate vicinity of a bomb, a reservoir of suppressant material, and transmission lines connecting the reservoir to the units. Each of the units provides for the transmission of a suppressant material, preferably water, therethrough. Each of the units has nozzles configured to disperse the suppressant material into the air surrounding the bomb. Preferably, the transmission occurs prior to the explosion of the bomb, and continues after the explosion as well. Each command-actuated unit preferably has associated therewith an adjustable flow rate, an adjustable flow pattern, and an adjustable droplet size. In one embodiment of the invention, the command-actuated units are stationary, while in another embodiment the units are mobile. A method for utilizing the system is also disclosed.

32 Claims, 10 Drawing Sheets

Fig. 9

Reduction in Shock Pressure

♦ Peak Incident Pressure

BLAST EFFECTS SUPPRESSION SYSTEM

BACKGROUND OF THE INVENTION

1. Field of the Invention

The present invention relates generally to a blast effects suppression system used to control the damage associated with explosive devices, and more particularly to a system which dispenses water or a similar substance in such a way as to limit the blast and incendiary damage to buildings and other structures, vehicles, and individuals from bombs, especially large vehicle bombs.

2. Description of Related Art

Terrorist acts often involve the use of explosive devices or bombs. One particularly damaging type of bomb is referred to as a large vehicle bomb (LVB). This type of bomb involves a large to extremely large explosive charge placed within a vehicle, such as a car or truck. The explosive charge may utilize any of a wide range of explosives, such as plastic explosives like Composition C4, cast explosives like TNT, or a mixture of ammonium nitrate and organic fuel. LVBs are often placed in proximity to important buildings, such as government buildings, buildings with high values in the eyes of the community, buildings containing critical assets, or inside parking structures.

Much of the damage associated with LVBs is related to the fact that a detonation or explosion creates what is known as air shock waves (also referred to as air shock) and air blast, and associated incendiary effects. Air shock are the very high speed initial shock waves in the form of a high amplitude, short duration compressive wave which moves radially outward through the air from the source of the explosion. The incident short-time pressure rise associated with air shock can be on the order of 10–10,000 or more pounds per square inch (psi), depending on the distance to the charge, and consequently can be very devastating to surrounding objects. The shock waves heat the air to hundreds or thousands of degrees. Furthermore, duration of this very damaging overpressure may be milliseconds or more, and significant impulse is associated with such a shock wave.

On the other hand, air blast can be described as the outward flow of air set in motion by the air shock waves, as well as large quantities of hot explosive products (gases and particulates) from the bomb. This form of overpressure can cause pressures in the range of from 10–1000 pounds per square inch to be reached in fractions of a second, with this overpressure being maintained for a notable duration of time. Secondary damage is also caused by bomb-generated debris and fragmentation, as well as the hot, expanding bomb gases and particulates known as the fireball.

The devastation associated with the explosive blast of LVBs is well known. For example, while a 2000 pound explosive weight truck bomb may generate a fireball 30 meters in diameter, a 5000 pound explosive weight truck bomb may generate a fireball 100 meters in diameter, and can damage structures even miles away. Due to the size of the explosive charge associated with LVBs, it can readily be appreciated that buildings and other permanent structures are severely damaged, not to mention the vehicles either parked or driving in the immediate vicinity of the bomb blast. Furthermore, due to the intensity of the blast, it is not uncommon for such explosions to result in the loss and maiming of human life.

Due to the potential severity of bomb damage, there have been numerous attempts at providing blast suppression systems. The approaches can be grouped generally into three categories. The first type of suppression system utilizes a frangible container positioned directly adjacent the bomb, with the container being filled with a bulk quantity of liquid, particularly water. When explosion occurs, the violence of the detonation breaks open the container thereby releasing the predetermined amount of liquid, which mixes with expanding explosion gases to limit overpressure and fireball effects. An example of this approach is disclosed in Barrett, U.S. Pat. No. 4,836,079.

However, the actual amount of suppressant which thoroughly interacts with the bomb is relatively small, thereby causing this method to be limited to smaller explosive devices due to the weight of, and setup time required to set in place, the requisite quantity of the selected suppressant. Additionally, there is significant expense associated with the manufacture and placement of such containers. Furthermore, utilization of this system normally requires at least some human exposure to the bomb, in order to place the containers, although robots can be used. Still further, this blast suppression mechanism operates post-incident, meaning that the blast suppression system only deploys due to an explosion.

The second type of suppression system involves a sensor-activated water or fire suppressant system. This type of system has been designed generally to suppress blast and incendiary effects from explosions resulting from the rapid combustion of liquid or gaseous fuel-type materials in enclosed areas, as opposed to the explosion or detonation of explosives in open or confined areas. Examples of this approach are disclosed in Bragg, U.S. Pat. No. 5,224,550, Cooper, U.S. Pat. No. 5,254,237, Sapko et al, U.S. Pat. No. 5,119,877, and Moore et al, U.S. Pat. No. 4,597,451.

However, the costs associated with such systems are prohibitively expensive when a large-scale protection of geographic areas of importance is attempted. Furthermore, in the event of an explosion, the blast effects happen too rapidly for such systems to feasibly react in time to effectively suppress them. Once again, the type of blast suppression is post-incident, meaning that the blast suppression system is activated and operates only after an explosion has actually occurred.

The third type of suppression system involves the generation and placement of a foam (usually aqueous) into the area containing the suspected explosive device. These foams are typically dispersions of water and a foaming agent, with water and entrapped air serving as the main active ingredients in the suppression system. Suspensions of water bubbles (films) and foam-carried droplets are known to be effective by interacting with the initial shockwave and by cooling the shocked air. Examples of this approach is disclosed in Moxon et al, U.S. Pat. No. 4,964,329, Clark et al, U.S. Pat. No. 4,589,341, and Graham et al, U.S. Pat. No. 4,543,872.

While, these foaming methods have produced good results, especially with relatively small bombs, the volume of foam needed for LVBs is a concern. The time required to create and maintain large volumes of foam can be considerable. Furthermore, the stability of such foam can easily be compromised by environmental conditions, such as temperature, wind or precipitation. Another problem unique to foam systems is that the presence of the foam obscures the actual bomb from view, thereby creating a more difficult situation for the bomb technicians. For example, for greatest effectiveness the foam must be placed on a specific suspect vehicle or package to reduce the damage from its explosion, thereby obscuring the object from view.

It is thus apparent that the need exists for a device or system for suppression of bomb blast effects, especially for large bombs such as LVBs, which overcomes the problems associated with the prior art. Such a device or system should be capable of being used in both the open-air and in enclosed structures, and should be able to be practically deployed in advance of a potential explosion near critical structures.

BRIEF SUMMARY OF THE INVENTION

There is disclosed a blast effects suppression system that creates a dynamic suspension of water droplets in air so as to interact with bomb explosive products and shock waves, which system includes one or more command-actuated units located in the immediate vicinity of high-value structures or areas, or other potential targets for bombs, a source of suppressant material, and transmission lines connecting the suppressant source to the units. These units could also be deployed as needed in the vicinity of a suspicious package or vehicle. Each of the units provides for the dispersion of a suppressant material therethrough and into the air surrounding a potential bomb and/or around a structure which is threatened by the suspect bomb.

Each of the units has nozzles configured to disperse the suppressant material into the air surrounding the bomb. The suppressant material when dispersed forms a plurality of droplets. The suppressant material may be dispersed in the form of a spray. Preferably, the transmission occurs prior to the explosion of the bomb, and can be manually or automatically initiated. Preferably, the base suppressant material is water or at least contains water. Each command-actuated unit preferably has associated therewith an adjustable flow rate, an adjustable flow pattern, and an adjustable droplet size.

In one embodiment of the invention, the command-actuated units are stationary, while in another embodiment the units are mobile. The suppressant material being dispersed at a given point in time has a weight, and the bomb associated therewith an explosive having a weight, with the ratio of the weight of the suppressant material to the weight of explosive being in the range of between 0.2 and 15, and more preferably being in the range of between 0.2 and 4. The invention additionally may include a sump. Thus, the suppressant may be recycled through the system.

There is also disclosed a blast effects suppression system which includes a source of suppressant material which is preferably water-based, a plurality of command-actuated units located in the immediate vicinity of a location that is susceptible to damage from a bomb, especially a LVB, and transmission lines connecting the suppressant source to the units, with the units providing for the transmission of the suppressant material therethrough, with the suppressant material being preferably water or water-based, and with each of the units having nozzles configured to disperse the suppressant material into the air surrounding a bomb, or around an asset or area, prior to the explosion of the bomb. The suppressant material when dispersed forms a plurality of droplets. The suppressant material may be dispersed in the form of a spray. Preferably, each of the units has a flow rate and flow pattern, both of which are adjustable.

In one embodiment of the invention, the command-actuated units are stationary, while in another embodiment the units are mobile. The nozzles can be configured to disperse the suppressant material into the air either around a critical structure or high value asset or inside an enclosed structure. The suppressant material being dispersed at a given point in time has a weight, and the bomb associated therewith an explosive having a weight, with the ratio of the weight of the suppressant material to the weight of explosive being in the range of between 0.2 and 15, and more preferably being in the range of between 0.2 and 4.

There is also disclosed a method of suppressing blast effects associated with a bomb or a suspected bomb, which method includes the steps of having the suspected bomb or bomb, or asset or area, surrounded by a plurality of command-actuated units with each of the units providing for the transmission of a suppressant material therethrough, and dispersing the suppressant material into the air surrounding the bomb or suspected bomb. The suppressant material when dispersed forms a plurality of droplets. The suppressant material may be dispersed in the form of a spray. Preferably, the suppressant material is dispersed prior to the explosion of the bomb. Preferably, the suppressant material continues to be dispersed for a time after the explosion. An additional step in the method involves the suppressant following dispersion being recycled for retransmission through the command-actuated units. The method preferably includes the step of adjusting the flow rate of the suppressant material, the step of adjusting the flow pattern of the suppressant material, and the step of adjusting the droplet size of the suppressant material.

Of course, it should be recognized that the nozzles may be configured to disperse the suppressant material into the air around a critical structure or high value asset, as well as around a suspect bomb. Furthermore, it should be recognized that the nozzles may be configured to disperse the suppressant material into the air inside an enclosed structure. When the method of this invention is utilized, the suppressant material being dispersed at a given point in time has a weight, and the bomb has associated therewith an explosive having a weight, with the ratio of the weight of the suppressant material to the weight of explosive being in the range of between 0.2 and 15, and more preferably in the range of between 0.2 and 4.

One objective of this invention is to provide a blast effects system for lessening the damage caused by explosions, particularly LVB explosions. An aspect of the invention is the creation of a dynamic suspension of water in the air near a critical structure and/or around a suspected bomb.

Another objective of this invention is to provide a blast effects system for significantly reducing peak shock strengths and overpressures as well as secondary blast and incendiary effects.

Yet another objective of this invention is to utilize a blast effects system which is activated pre-incident.

Still another objective of this invention is the using of a recyclable suppressant material.

Other aspects and advantages of the instant invention will be appreciated from the following description, drawings, and the appended claims.

BRIEF DESCRIPTION OF THE DRAWINGS

FIG. 9 discloses a graph demonstrating at relatively low ratios of weight of spray to weight of explosive the reduction in shock pressure associated with the initial incident air shock-wave from an explosion when the system of this invention is in use.

DETAILED DESCRIPTION OF THE INVENTION

Figure 1:
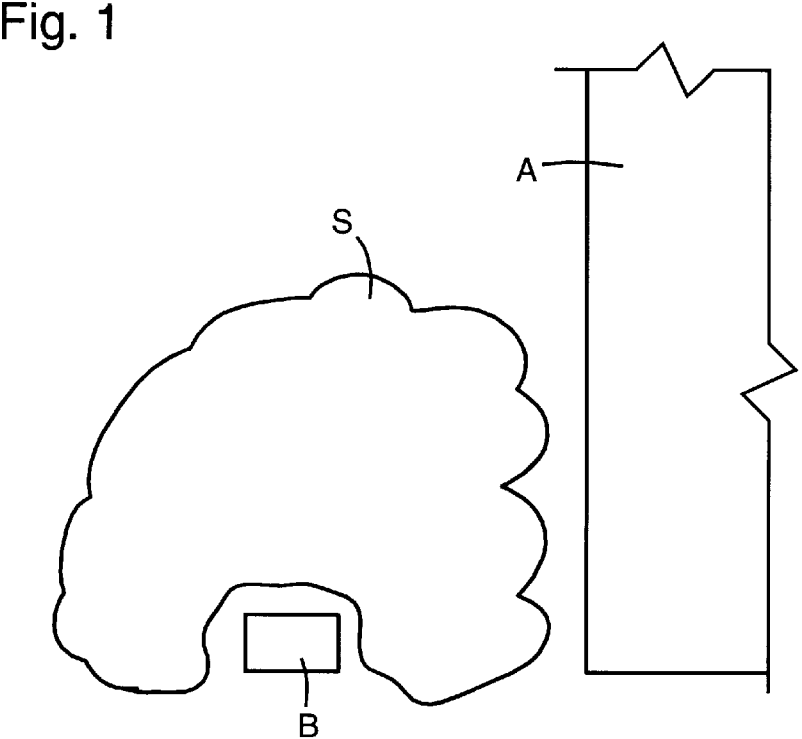
FIG. 1 discloses a schematic view of a dynamic suspension of a suppressant, such as water, into the air around a suspected bomb and/or a high-value asset.

Having reference to the drawings, attention is directed first to FIG. 1 which shows a schematic of a dynamic suspension of suppressant material such as water S in air around a bomb B and in the vicinity of high value assets A, such as a building, thus disclosing the general concept of the invention. It is the unique concept of positioning a dynamic suspension of water in the air surrounding a bomb or other explosive device which is the invention. The degree of destruction associated with bomb blasts and in particular LVB's has been discussed above. The effectiveness of this invention will aid in the preservation of high value assets such as buildings, as well as human life unable to get sufficiently far away from the blast's origin.

Figure 2:
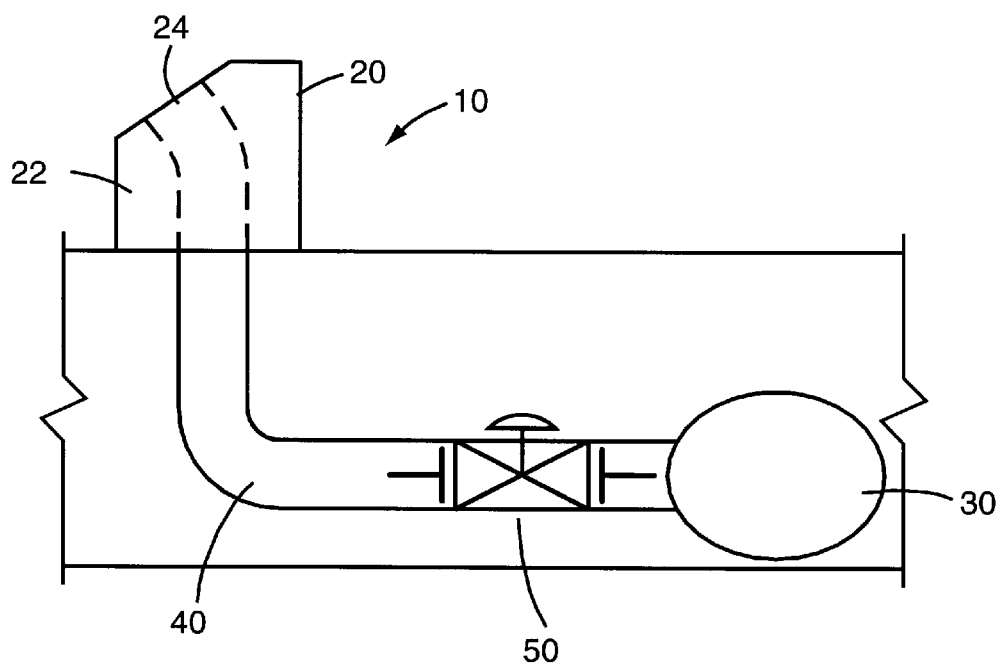
FIG. 2 discloses a schematic view of the blast effects suppression system associated with the present invention.

FIG. 2 discloses one embodiment of the invention of the blast effects suppression system associated with this present invention generally disclosed by the numeral 10. For purposes of this invention, the words "explosion", "blast" and "detonation" are all intended to be interchangeable, unless otherwise defined, and to describe the dynamic, damaging effects of bomb functioning.

The system 10 has as its basic components a plurality of command-actuated units 20, a suppressant source 30, such as a high pressure line such as a hydrant, a standpipe, a pump, a portable or permanent tank, or a body of water such as a reservoir, and transmission lines 40 connecting the suppressant source to the command-actuated units. The suppressant source 30 can be a tank containing the suppressant, or part of a larger supply system, such as a city's water supply. Whether an existing supply system is used or modified to accommodate this invention, the transmission lines 40 are of the type already known in the art as being able to transport fluids such as water. They may be metal, plastic, standard fire hose construction, or concrete.

A valve 50, such as an electromechanical, hydraulic, or pneumo-mechanical valve can be connected via electrical cable to a security command center, with the valve being designed to be actuated from the command center when a suspicious vehicle or other form of suspect bomb is spotted in an area targeted by the blast effects suppression system of this invention. The security command center would not necessarily have to be at the protected site. Operation of the system from a remote location would be beneficial in minimizing the number of unevacuated persons from the area, by making sure that security personnel would be kept clear of potentially dangerous sites, and by allowing emergency response personnel to have complete control over the suppression system. The valving mechanism may be operated by either manual valve movement, remote control activation, by a sensor such as a fire sensor, a vehicle weight sensor, by some unspecified explosives-substance sensor which would automatically detect the presence of a suspect bomb such as by sensing explosive residue, or a sensor which detects a suspicious package or vehicle in a controlled access or patrolled area.

It can thus be appreciated that the system has a design such that it can be upgraded to include a greater area of protection or increased automation and control. One such upgrade would be for the system to recycle a portion of the suppressant material while operating at the same time to disperse the suppressant, by draining already dispersed suppressant material into a sump and then having the reclaimed suppressant recycled through the system for redispersion. The system as thus modified would be able to provide a higher flow rate than what otherwise might be able to be provided by the existing infrastructure. It is also believed that the system as thus modified would be able to sustain a high flow rate for a longer period of time than some unmodified systems.

Another modification of the invention would be to provide for a system featuring continuously running programmable fountains, especially ones with the aforesaid recycling feature. Such fountains would be programmable to place a voluminous dispersion between the suspect bomb and the object to be protected. Although in the preferred embodiment of the invention, the system of this invention is most effective when the suppressant is very close to, even surrounding, the bomb, the effects of any explosion can be lessened provided the suppressant is dispersed in the air intermediate the bomb and the object to be protected. The embodiment of the invention disclosed in FIG. 2 features stationary command-actuated units, whereas the embodiment of the invention disclosed in FIG. 3 features mobile command-actuated units. The structures may be formed of concrete, cement, metal, or some other composition so that the units can withstand some forms of vandalism, some forms of criminal damage such as small bomb attacks, or some forms of damage due to vehicle impact. Meanwhile, the embodiment of the invention disclosed in FIG. 4 features command-actuated units contained within another structure, such as a building, as opposed to being free-standing themselves, such that the units are protected from tampering or sabotage. Thus, the command-actuated units can continue to function as a deliverer of suppressant after the detonation of an explosive device, so that any resultant fires can be contained.

In the preferred embodiment of the invention as shown in FIG. 2, each command-actuated unit 20 is pre-emplaced so as to be stationary. Each unit 20 is formed having a base member 22 and at least one nozzle 24. The nozzle 24 can be of the smooth bore, high-flowrate type associated with fire fighting equipment, and preferably is of the type which can vary droplet size and flow pattern. The nozzle could also be a large-capacity fog nozzle. As discussed below, in the preferred embodiment of the invention a combination of the nozzles are used. While the base member 22 is shown as resting on the ground, it should be appreciated that the base member could be installed so as to be flush with the ground by being recessed, or be disguised to prevent individuals from becoming aware of its presence. To ensure proper supply to the nozzle, additional pumps may be required.

Figure 3:
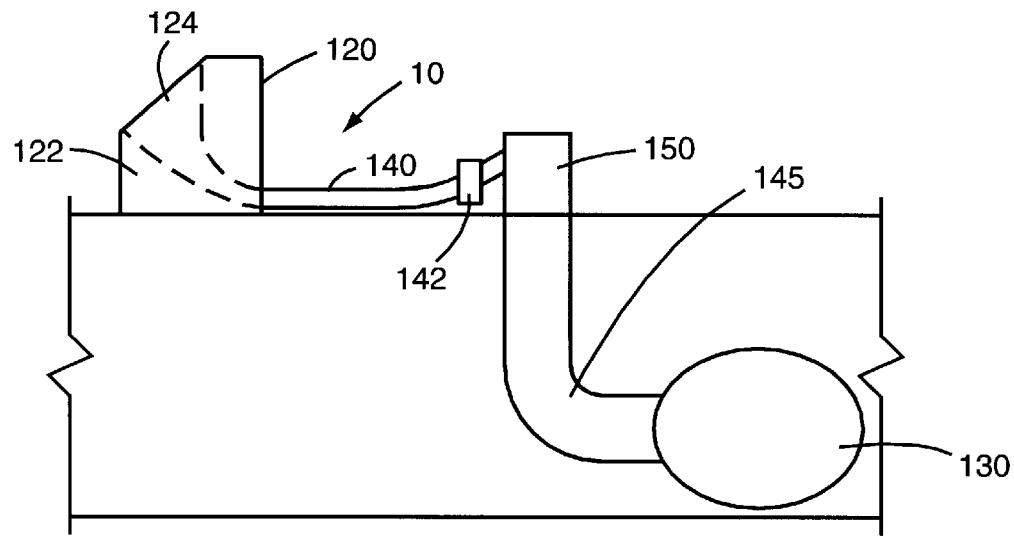
FIG. 3 discloses a schematic view of a modified embodiment of the invention.

In the modified embodiment of the invention as shown in FIG. 3, each command-actuated unit 120 is mobile, having a base member 122 and at least one nozzle 124. These mobile units can be pre-emplaced to protect an area or installed on relatively short notice in order to respond to a threatening condition. Once again, the nozzle 124 can be of the high-flowrate type associated with fire fighting equipment or a large-capacity fog nozzle, and preferably is of the type which can vary droplet size and flow pattern. The command-actuated unit is connected preferably via a hose 140 similar to fire hose to an existing hydrant 150, which acts as a valve, and which in turn is connected to additional transmission lines 145, which are connected to a suppressant source 130. If the system is one which is dedicated, and hence not used for fighting fires, it is desirable to have a pump 142 located downstream from the hydrant and connected to the hose 140, in order to have sufficient pressure. If the pressure of the system is sufficiently high, then a pump 142 is not required.

Figure 4:
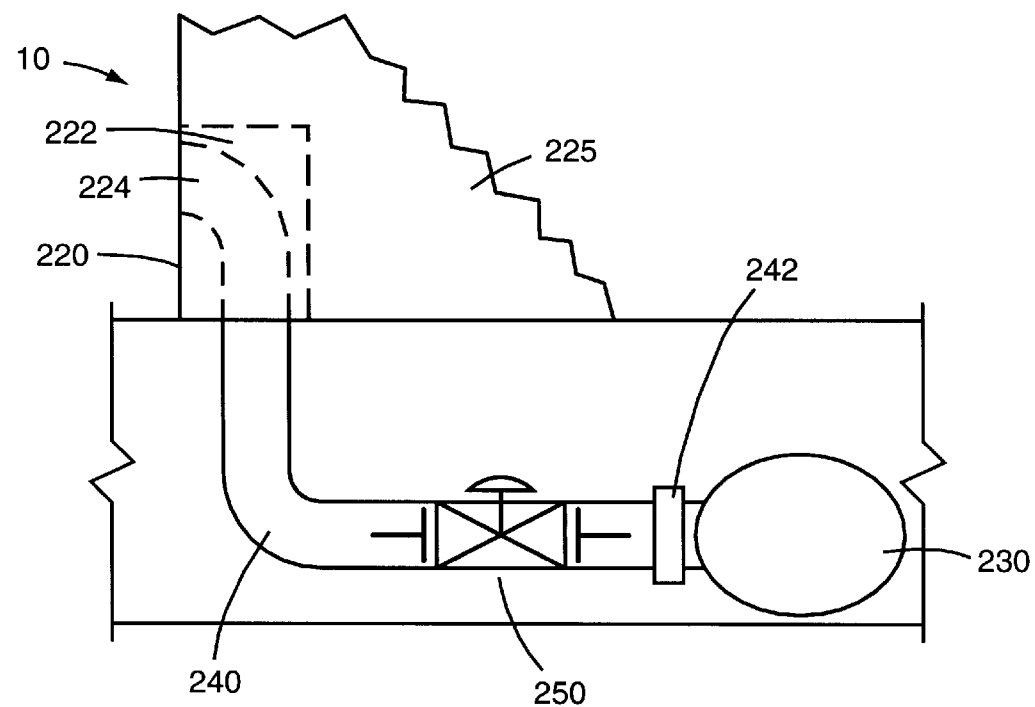
FIG. 4 discloses a schematic view of another modified embodiment of the invention.

In the other modified embodiment of the invention as shown in FIG. 4, each command-actuated unit 220 is contained in another structure such as a building or barricade 225. Once again each command-actuated unit has a base member 222 and at least one nozzle 224. The nozzle 224 can be of the high-flowrate type associated with fire fighting equipment or a large-capacity fog nozzle, and preferably is of the type which can vary droplet size and flow pattern. The command-actuated unit is connected preferably via a transmission line 240, which in turn is connected to a suppressant source 230. If the system is one which is dedicated, and hence not used for fighting fires, it is desirable to have a pump 242 located downstream from the hydrant and connected to the hose 240, in order to have sufficient pressure. If the pressure of the system is sufficiently high, then a pump 242 is not required. A valve 250 can also be present, but may not be needed if a pump is present.

Other additional components which could be incorporated into the system of this invention include pressure boost pumps to extend the range of the protected volume of suppressant material, a suppressant reclamation system to allow for longer continuous operation of the system, additional nozzles or spray units to enhance system flexibility, and barriers to prevent the disablement of existing deployed command-actuated units.

In actual use, the system of this invention can be pre-deployed or quickly deployed in a purposefully designed pattern at or near a place or asset threatened by explosive or explosive-incendiary devices and their effects. Preferably, the flow rate, flow pattern, and droplet size can be adjusted to maximize the effectiveness of the invention. For example, the system could be sensor-adjusted, such that windage sensors could adjust the direction and/or droplet size of the dispersed suppressant material to maintain proper coverage of the selected area, or machine vision sensors could adjust the direction of the suppressant sprays to follow a moving vehicle or item.

By causing the suppressant material to be transmitted through supply lines, the bomb is effectively surrounded by a dynamic suspension of the suppressant material. The dynamic suspension preferably has no pockets or gaps therein. In the case of the preferred embodiment of the invention, the blast effects suppression system of this invention can be deployed in less than one minute from the time the command center identifies the location of a supposed explosive device.

For example, when a suspect vehicle or object is determined to be in an area that potentially threatens an important facility, the suppression system of this invention is turned on. This action starts the pump and opens the appropriate valves (if applicable) so that the spray nozzles begin to receive the proper flow of suppressant. The nozzles are arranged in such a way as to maximize the effectiveness of the suppressant material. An example of such a highly efficient arrangement would be where a series of smooth bore nozzles project approximately 75% of the suppressant to a height of approximately 50 feet with the suppressant landing on the area directly surrounding the LVB. In such a system, the smooth bore nozzles would be positioned approximately 150–250 feet from the LVB. The remaining 25% of the suppressant would be projected through a few large-capacity fog nozzles to a height of approximately 30 feet to provide a wide curtain of suppressant material of relatively small droplet size. In such a system, the fog nozzles would be positioned approximately 30–40 feet from the LVB.

The design of combining the smooth bore nozzles with the fog-type nozzles has been found to be the most effective method of suppressing both the peak pressure of the blast and the impulse at the same time. This is because the two types of nozzles provide different types of suppressant dispersion. In order to suppress the peak pressure, a spatially-thick, high heat capacity media of discontinuous density is needed. This situation is provided by using the aforesaid combination of nozzles to generate a combination of many small droplets directly adjacent an LVB, along with a greater volume of larger droplets with greater spaces therebetween. The impulse is further reduced by the interaction with, and heat transfer to, the bulk mass of suppressant material found in residual spray from the smooth bore nozzles.

The spray patterns depicted in the drawing figures of this invention show typical coverage of one outdoor suppression system. The output of one command-actuated unit can be between 1,000–8,000 gallons per minute, although it is believed that an output of around 4,000 gallons per minute is preferred, with such output suspending approximately 1,800 pounds of suppressant in the air at any one time. The output would be modified to suit the unique site conditions. For example, multiple units would be used for a larger vehicle.

Figure 5:
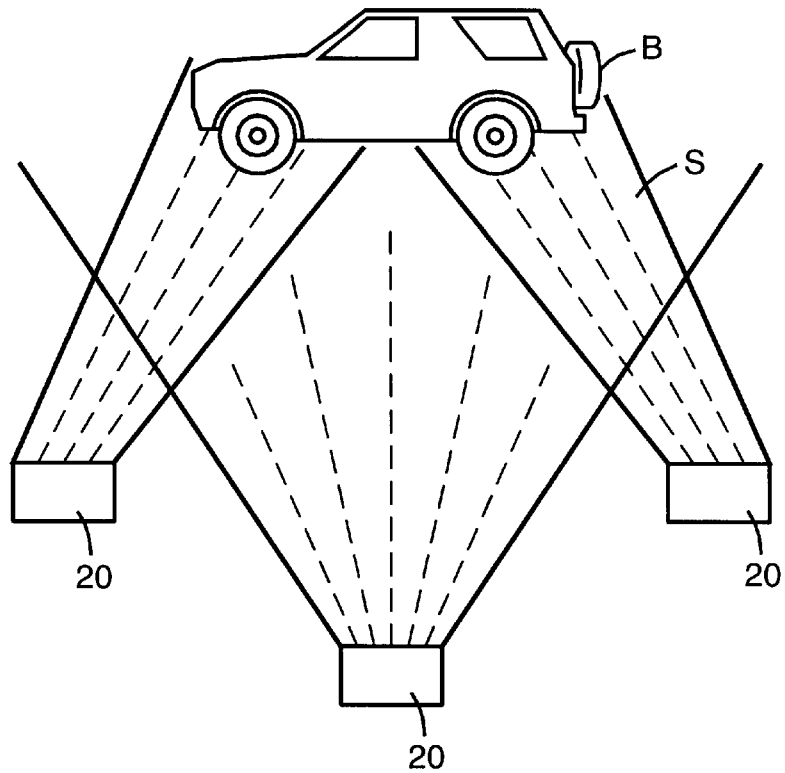
FIG. 5 discloses a schematic showing the invention in one form of operation.
Figure 6:
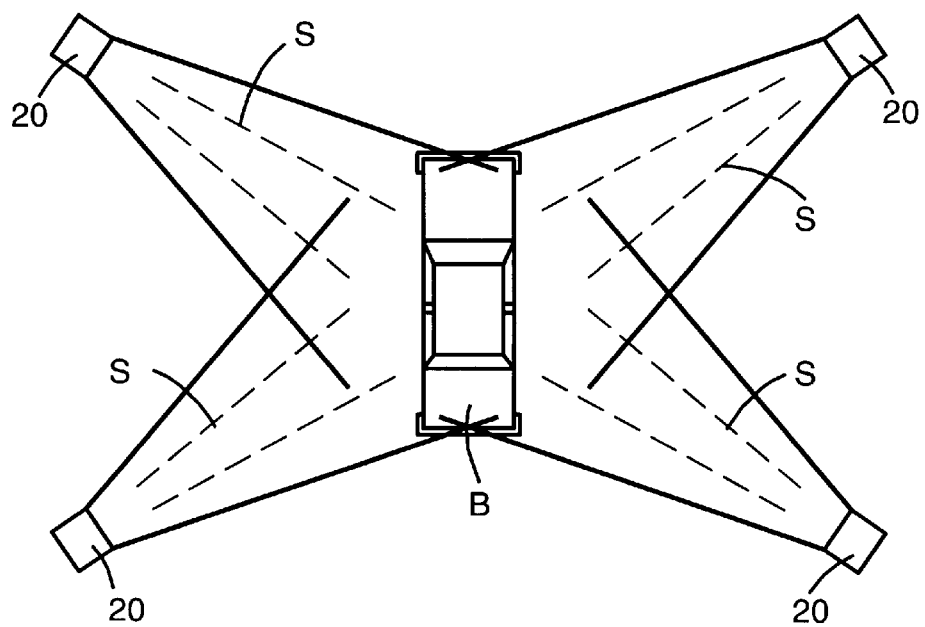
FIG. 6 discloses a schematic showing the invention in another form of operation.
Figure 7:
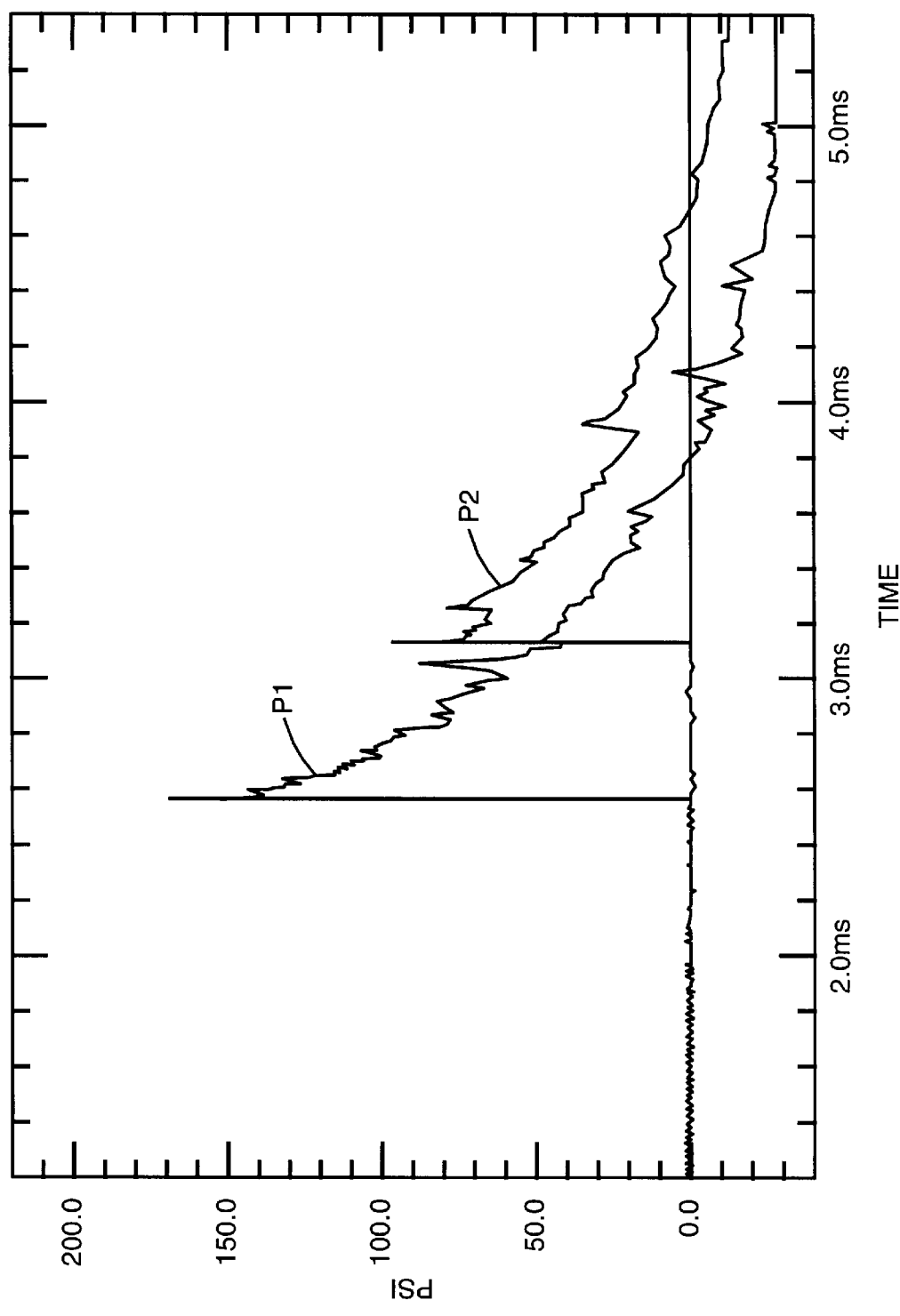
FIG. 7 discloses a graph demonstrating the reduction in the damaging overpressure effects associated with an explosion when the system of this invention is in use.

FIGS. 5 and 6 disclose schematics showing the invention in operation using two different spray patterns. In FIG. 5, the blast is suppressed primarily from one side, while in FIG. 6, the blast is suppressed from all sides. Thus, it should be appreciated that the precise placement of command-actuated units can change and will in some cases be tailored to the specific sites or applications. In both drawing figures, due to the presence of the spray generally around the bomb, for purposes of this invention the bomb is referred to as being surrounded, thus the command-actuated units do not have to completely encircle the suspected bomb as is shown in FIG. 6. While the system of this invention could theoretically function with a single unit, preferably a plurality of command-actuated units are utilized, with a preferred number believed to be between three and six. As the suppressant material S is forced out under pressure through the plurality of nozzles associated with the plurality of command-actuated units 20, the entire desired air-space volume is filled with the suppressant material in a properly dispersed state as the nozzles are configured to provide for maximum dispersion of the suppressant material about the bomb B. Ideally, the spray of suppressant material is centered over the bomb location.

When the explosion occurs, the shock wave loses significant energy as it passes through the envelope of suppressant material. This causes it to slow, and weaken due to a lower overpressure rise and less shock heating of the air. Further, as the shocked air interacts with the droplets, it is cooled, reducing its pressure. In addition, the outward velocity of the shocked air is reduced, thereby lowering the dynamic pressure. When the hot explosion products from the bomb mix with the water-laden air, their temperature is reduced, and their combustion with oxygen in the air is lessened. For a bomb in an enclosed area, such as a parking garage, the reduction of these effects as well as quasi-static overpressure is also of great value. Overall the radiant heat and the incendiary effect associated with the blast is lessened in addition to reducing the effective intensity of the explosion. This decrease in intensity consequently decreases the damage associated with the blast, by the reduction in incident (static and reflected) and dynamic overpressure and their associated impulses. The system of this invention may also be redirected, especially with the more portable command-actuated units, so as to provide fire suppression capability.

Alternatively, the system may be activated to envelope the bomb until such time as the vicinity around the bomb has been evacuated. Once evacuation is complete, the flow of suppressant material can be turned off, thereby permitting unobstructed approach to the suspect vehicle by explosive ordnance disposal personnel. Similarly, a structure threatened by a suspect bomb (package or vehicle) can be protected by the water suspension until evacuated, then the system could be turned off.

Although it is anticipated that the suppressant material S shown in FIG. 5 will be water, other components could be added. Water is desirable because of its high heat of vaporization, and high specific heat capacity. The presence of the water droplet suspension causes the shock wave to weaken rapidly as it travels, and also cools the shock heated air. Further, it slows the velocity of shock-accelerated air thereby reducing the dynamic blast overpressure. Still further, it cools expanding explosion products, thereby reducing the size, overpressure, and incendiary effects of the fireball. Further, water is inert, has a relatively low cost associated therewith, is easy to deliver, and has a high specific heat capacity. With respect to the aforementioned additives, the freezing point or viscosity of the suppressant material may be changed due to utilization of appropriate additives such as certain salts, ethylene glycol or propylene glycol. Furthermore, additives to cause the suppressant material to partially foam could be used if deemed necessary.

The effectiveness of the system of this invention in reducing the energy given off by an explosion when the system of this invention is in use can best be appreciated by comparing FIGS. 7–13. For example, FIG. 7 discloses a graph demonstrating the effectiveness reduction in the damaging overpressure effects given off by an explosion when the system of this invention is in use. This graph illustrates the comparison between the energy given off by a blast not using the blast effects suppression system of this invention and a blast using the same amount of explosive, but which blast utilizes the suppression system of this invention. In actuality, the test was conducted using ten pounds of ammonium nitrate and fuel oil at a distance of ten feet from a gauge to measure the reflected pressure of the explosion, with the gauge having a piezo-resistive transducer.

The graph shows an overpressure versus time plot. The baseline curve, P1, illustrates the overpressure effects when the invention is not in use, while pressure reduced curve, P2, illustrates the energy when the invention is in use. It can readily be appreciated that both peak shock and impulse (the total area under the curve) are significantly reduced. Additionally, it will be seen that there is less negative phase associated with utilization of the invention. It also can be seen that the peak shock did not impact the gauge as quickly when the invention was being utilized. With further refinement, it is hoped that peak shock will be reduced by 70%, and impulse will be reduced by 80%.

Figure 8:
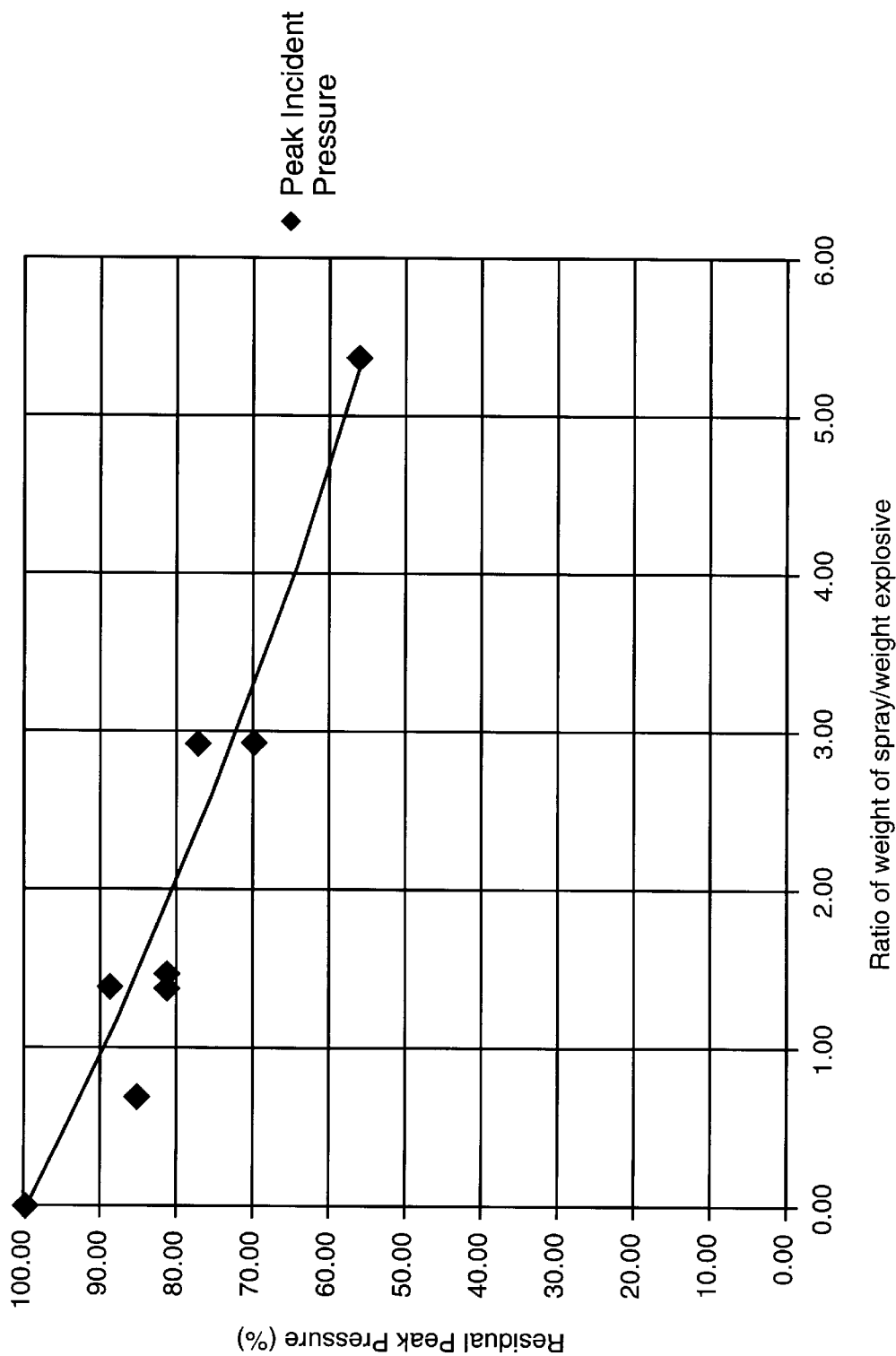
FIG. 8 discloses a graph demonstrating the reduction in shock pressure associated with the initial incident air shock-wave from an explosion when the system of this invention is in use.

FIGS. 8–13 show the measurement of pressure variance versus time at a given point in space. For example, FIGS. 8 and 9 disclose graphs demonstrating the reduction associated with the shock pressure given off by an explosion when the system of this invention is in use. The percentage of residual peak pressure is equal to the peak incident pressure associated with a given explosion when the invention is in use as compared to the baseline peak incident pressure when the invention is not in use. Thus, from viewing these two drawing figures it will be readily appreciated that as the ratio of the weight of the spray to the weight of the explosive increases, the peak incident pressure dramatically decreases. In FIG. 8, the tests were conducted using a low trajectory spray from two high flow-rate fog nozzles aimed almost directly at the explosive charge. As the ratio of the weight of the spray to the weight of the explosive goes from zero to slightly more than 5:1, the residual peak pressure decreases by slightly more than 40%. As the shock pressure decreases, so too does the damage caused by the explosion.

Figure 9:
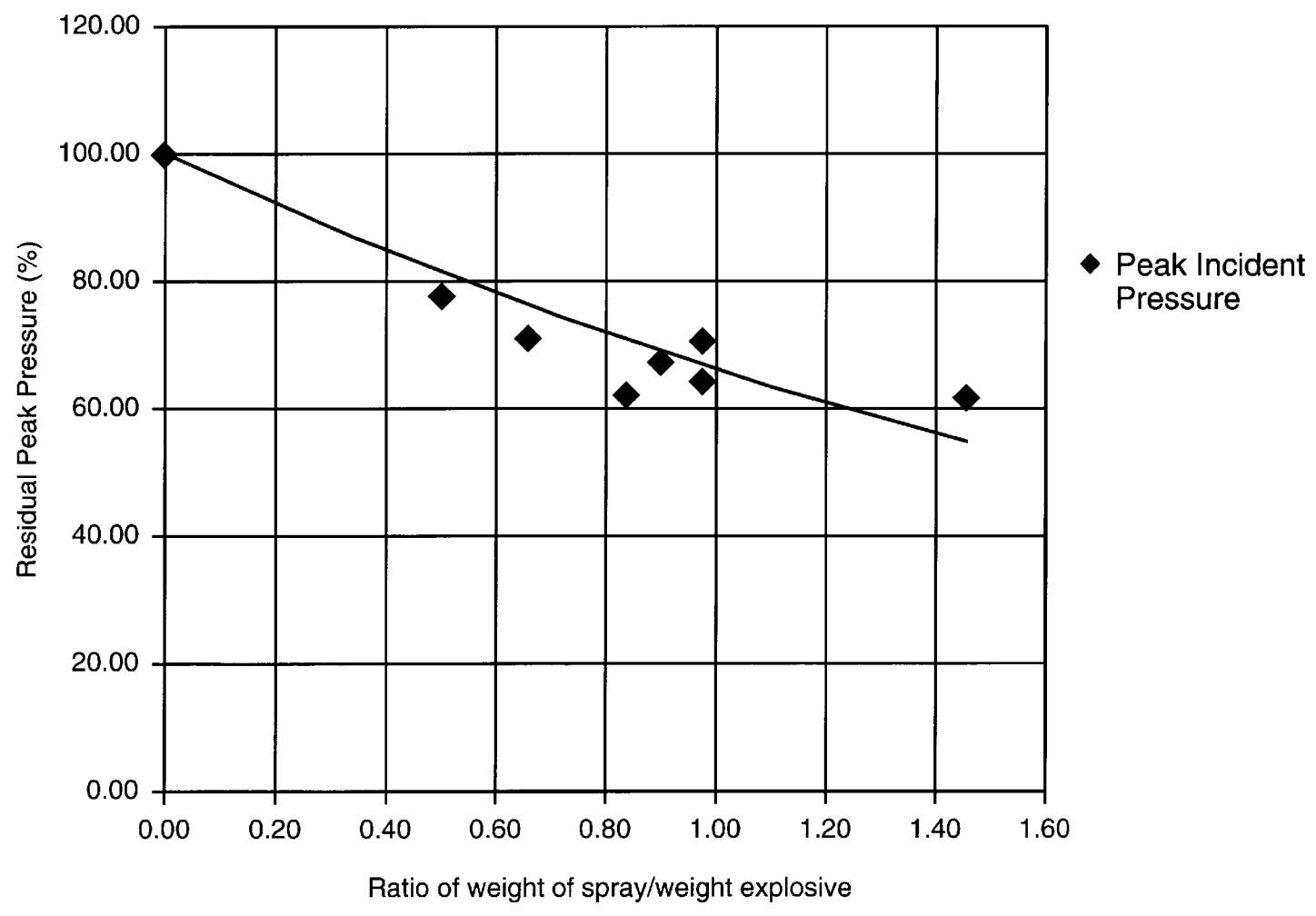

In FIG. 9, the tests were conducted at a lower pressure, but using pipes with holes such that a high trajectory was achieved. Although the same amount of water was used for each test as was used for the tests shown in FIG. 8, the dispersion of water effectively surrounded the charge to a greater degree. This can be appreciated when it is noted that as the ratio of the weight of the spray to the weight of the explosive goes from zero to slightly more than 1.4:1, the residual peak pressure decreases by slightly more than 40%. Whereas, in FIG. 8 the peak pressure decreased by less than 20% over the same range.

Figure 10:
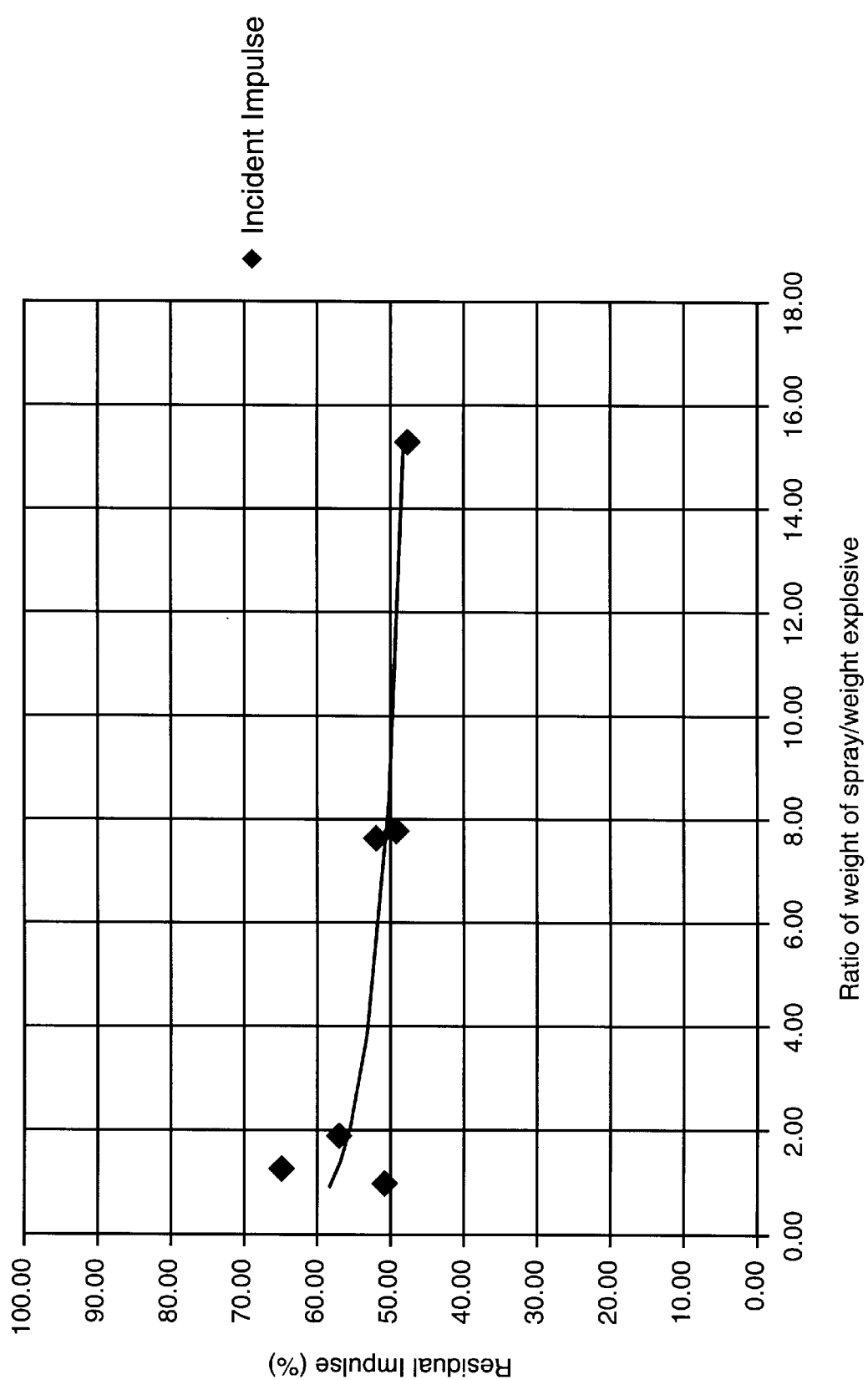
FIG. 10 discloses a graph demonstrating the reduction in impulse associated with the incident air shock wave from an explosion when the system of this invention is in use.

FIG. 10 discloses a graph demonstrating the reduction in impulse associated with an explosion when the system of this invention is in use. In FIG. 10 as in FIG. 8, the tests were conducted using a low trajectory spray from two high flow-rate fog nozzles aimed almost directly at the explosive charge. In FIG. 10, it can be readily appreciated that there is a reduction in incident impulse as the ratio of the weight of the spray to the weight of the explosive increases. As the ratio of the weight of the spray to the weight of the explosive goes from near zero to slightly more than 15:1, the residual impulse shows a decrease to slightly more than 50%. Associated with this reduction in incident impulse is a decrease in the damage caused.

Figure 11:
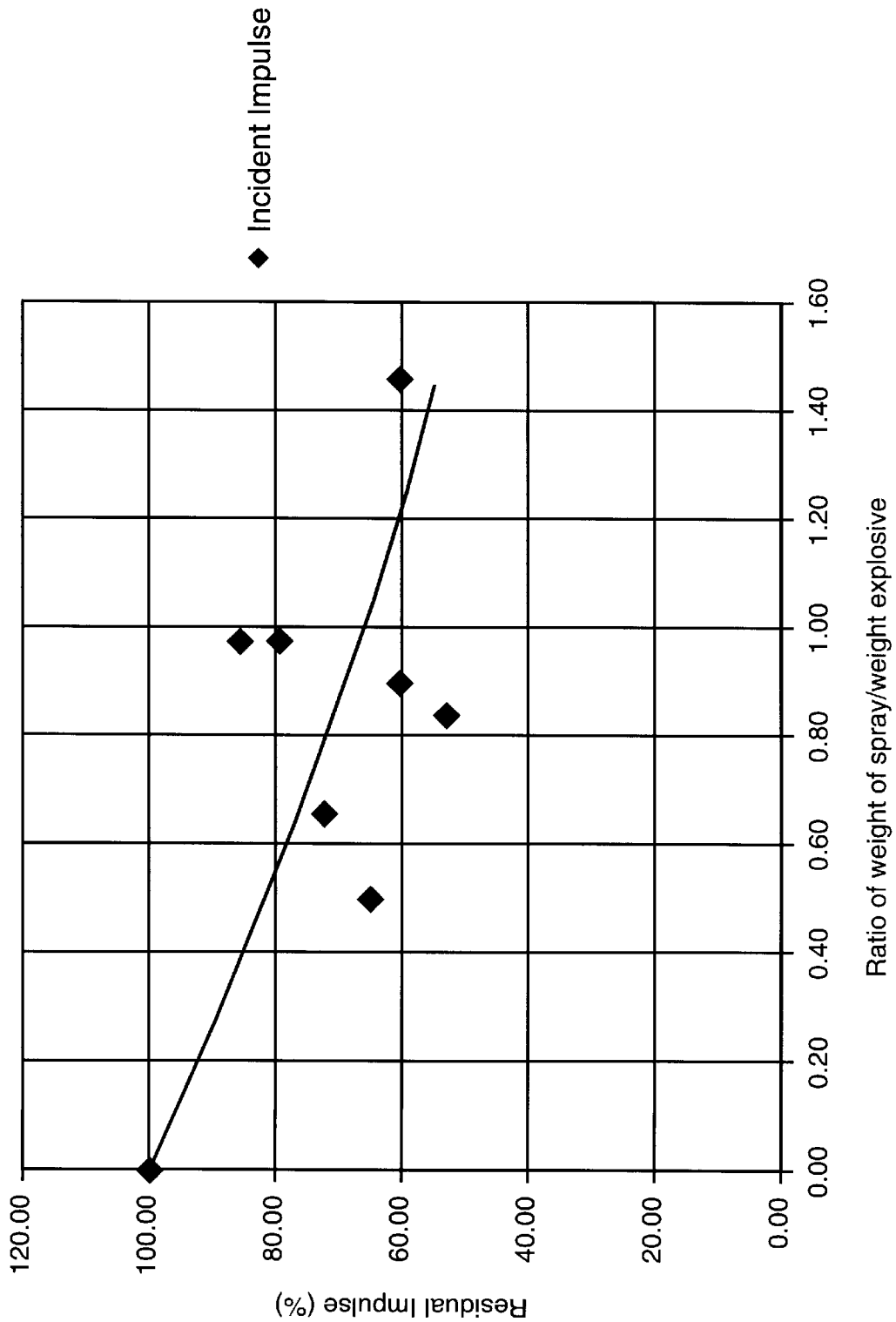
FIG. 11 discloses a graph demonstrating at relatively low ratios of weight of spray to weight of explosive the reduction in impulse associated with the incident air shock wave from an explosion when the system of this invention is in use.

In FIG. 11 as in FIG. 9, the tests were conducted at a lower pressure using pipes with holes such that a high trajectory was achieved. Although the same amount of water was used for each test as was used for the tests shown in FIG. 10, the dispersion of water effectively surrounded the charge to a greater degree. This can be appreciated when it is noted that as the ratio of the weight of the spray to the weight of the explosive goes from zero to slightly more than 1.4:1, the incident impulse decreases by slightly more than 40%.

While the overall graph is believed to be fairly accurate, it will be appreciated that the specific readings fall both above and below the line. Most interestingly, it will be noted that the readings for ratios between 0.80 and 0.90 exhibit more than a 40% reduction in impulse, while the readings for ratios between 0.95 and 1.00 exhibited no more than a 20% reduction. There is an explanation for this, namely, droplet size. When embodiments of the invention were initially being developed, the droplet size was not thought to be that important. However, FIG. 11 surprisingly demonstrates that such is not the case. The former two readings discussed above were taken in connection with tests where the droplet size was relatively small compared to the latter two tests discussed above where the droplet size was much larger. It is thought that the smaller droplet size, and thus the resultant greater number of the smaller drops, permitted the greater surface area associated with the greater number of drops to absorb more of the incident impulse than was possible with the relatively smaller number of bigger drops.

Comparing the data of FIGS. 8–11 reveals that a ratio in the weight of spray to the weight of explosive of 0.2–15 produces advantageous results. More importantly from a cost-effectiveness standpoint, a ratio in the weight of spray to the weight of explosive of 0.2–4 produces advantageous results that do not also require an unusually large volume of water in comparison with the result achieved.

FIGS. 12 and 13 disclose graphs demonstrating the reduction in quasi-static pressure associated with an explosion when the system of this invention is in use. Quasi-static pressure equals the total energy output associated with a particular explosion. For the tests shown in the graphs associated with this invention, the quasi-static pressure was recorded over a time period of approximately 1.5 seconds, as compared to the approximately 10 milli-second time period shown associated with the reflected pressure shown recorded in FIG. 7.

In FIGS. 12 and 13, it can be readily appreciated that there is a reduction in quasi-static pressure as the ratio of the weight of the spray to the weight of the explosive increases. In each of these series of tests, the gauges to measure the quasi-static pressure associated with each explosion were placed ten feet from the explosive. In the tests associated with FIG. 12, the suppressant was sprayed at the explosive device similar to the pattern shown in FIG. 6. The nozzles were located eighteen feet from the explosive. More importantly, the nozzles were of the fog-nozzle type, such that due to the distance, the water was sprayed almost directly at the explosive, such that the suppressant when dispersed did not have much height associated therewith. It will be noted that as the ratio of the weight of the spray to the weight of the explosive goes from near zero to slightly more than 15:1, the residual pressure shows a decrease of between 40–45%. Once again, associated with this reduction in quasi-static pressure is a decrease in the damage caused.

In the tests associated with FIG. 13, the suppressant was sprayed at the explosive device similar to the pattern shown in FIG. 5, essentially from only one side. Furthermore, instead of using fog nozzles, the pipes with holes therein were used, with the pipes being three, four, and five feet from the explosive. In these series of tests, the water was sprayed almost directly up into the air. It will be noted that as the ratio of the weight of the spray to the weight of the explosive goes from near zero to slightly more than 1.4, the residual pressure shows a decrease of over 80%, with many of the actual test results showing a reduction in residual pressure of between 70–75%.

At first glance, these results were considered to be somewhat surprising given the fact that the suppressant in the tests associated with FIG. 12 was coming from more than essentially one side of the explosive. However, upon further reflection, it is thought that there may be two reasons for the improved results associated with FIG. 13. First, the use of fog nozzles in the tests associated with FIG. 12, precluded greater dispersion of the suppressant given the spatial constraints associated with the tests. Second, as discussed above, in the tests done in connection with FIG. 12, the suppressant when dispersed did not have much height, whereas in the tests done in connection with FIG. 13, the volume of suppressant surrounding the explosive had a greater height. For these reasons, the overall conditions of the tests of FIG. 13 demonstrate a greater efficiency of reduction in the quasi-static pressure. Also once again, associated with this reduction in quasi-static pressure is a decrease in the damage caused.

The present invention thus provides a system and method for blast effects suppression which decreases the damage associated with explosive blasts, especially those caused by LVBs. It can be easily assembled due to its being made with many existing components. It can be used to suppress the effects of a specific suspect bomb (package or vehicle) or the effects of a bomb on a specific structure, enclosed area or open area. It can also almost immediately be turned off, to give those first responding a clear view of the area, unlike with aqueous foams. An attendant advantage associated with the system is the ability to recycle the suppressant material. This is especially true when the suppressant material is predominately water.

While the blast effects suppression system and method of using such system herein described constitutes the preferred embodiment of the invention, it is to be understood that the invention is not limited to this precise form of blast effects suppression system or method of suppression of blast effects and that changes may be made therein without departing from the scope of the invention which is defined in the appended claims.

What is claimed is:

1. A blast effects suppression system to interact with the explosive blast when an explosion occurs comprising a plurality of command-actuated units located in the vicinity of potential bomb damage to high-value structures or in the vicinity of potential bomb damage to other potential targets for bombs, each of said units providing for the transmission of a suppressant material therethrough, each of said units having nozzles configured to disperse said suppressant material into the air where blast effects are to be suppressed, a source of said suppressant material, and transmission lines connecting said source to said units.

2. The system according to claim 1, wherein said transmission of suppressant material occurs prior to the explosion of the bomb whose blast effects are to be suppressed.

3. The system according to claim 2, wherein said suppressant material being dispersed at a given point in time has a weight, and the bomb has associated therewith an explosive having a weight, with the ratio of the weight of the suppressant material to the weight of explosive being in the range of between 0.2 and 15.

4. The system according to claim 2, wherein said suppressant material being dispersed at a given point in time has a weight, and the bomb has associated therewith an explosive having a weight, with the ratio of the weight of the suppressant material to the weight of explosive being in the range of between 0.2 and 4.

5. The system according to claim 1, wherein said suppressant material contains water.

6. The system according to claim 1, wherein said units are stationary.

7. The system according to claim 1, wherein said units are mobile.

8. The system according to claim 1, wherein said suppressant material when dispersed forms a plurality of droplets.

9. The system according to claim 1, wherein said suppressant material when dispersed is dispersed in the form of a spray.

10. The system according to claim 1, wherein each of said units has a flow rate and flow pattern, both of which can be adjusted.

11. The system according to claim 1, which includes a sump.

12. The system according to claim 1, wherein said suppressant is recycled through said system.

13. The system according to claim 1, wherein said suppressant material continues to be dispersed for a time after the explosion.

14. A blast effects suppression system comprising
    a plurality of command-actuated units located in the vicinity of potential bomb damage to high-value structures or in the vicinity of potential bomb damage to other potential targets for bombs, each of said units providing for the transmission of a suppressant material therethrough, said suppressant material being water, each of said units having nozzles configured to disperse said suppressant material into the air surrounding the suspected bomb prior to the explosion of the bomb, each of said units having a flow rate and flow pattern which is adjustable,
    a source of said suppressant material, and
    transmission lines connecting said source to said units.

15. The system according to claim 14, wherein said units are stationary.

16. The system according to claim 14, wherein said units are mobile.

17. The system according to claim 14, which includes units having nozzles configured to disperse said suppressant material into the air around a critical structure or high value asset.

18. The system according to claim 14, which includes units having nozzles configured to disperse said suppressant material into the air inside an enclosed structure.

19. A method of suppressing blast effects associated with a suspected bomb located in or adjacent to a building, so that the bomb blast will not damage the building, the method comprising the steps of
    having the suspected bomb surrounded by a plurality of command-actuated units, each of said units providing for the transmission of a suppressant material therethrough, said suppressant material interacting with the explosive blast when an explosion occurs, and
    dispersing said suppressant material into the air surrounding the suspected bomb.

20. The method according to claim 19, in which said suppressant material is dispersed prior to the explosion of the suspected bomb.

21. The method according to claim 19, in which said suppressant material continues to be dispersed for a time after the explosion.

22. The method according to claim 19, which includes the step of adjusting the flow rate of said suppressant material.

23. The method according to claim 19, which includes the step of adjusting the flow pattern of said suppressant material.

24. The method according to claim 19, which includes the step of adjusting the droplet size of said suppressant material.

25. The method according to claim 19, wherein said suppressant material being dispersed at a given point in time has a weight, and the suspected bomb has associated therewith an explosive having a weight, with the ratio of the weight of the suppressant material to the weight of explosive being in the range of between 0.2 and 15.

26. The method according to claim 19, which includes the additional step of having the suppressant once dispersed then being recycled for transmission again through the command-actuated units.

27. A blast effects suppression system comprising
    a plurality of command-actuated units located in the vicinity of potential bomb damage to high-value structures or areas, or in the vicinity of potential bomb damage to other potential targets for bombs, each of said units providing for the transmission of a suppressant material therethrough, said transmission of suppressant material occurring prior to the explosion of the bomb whose blast effects are to be suppressed, each of said units having nozzles configured to disperse said suppressant material into the air where blast effects are to be suppressed, said suppressant material being dispersed at a given point in time having a weight, and the bomb has associated therewith an explosive having a weight, with the ratio of the weight of the suppressant material to the weight of explosive being in the range of between 0.2 and 15,
    a source of said suppressant material, and
    transmission lines connecting said source to said units.

28. A blast effects suppression system comprising
    a plurality of command-actuated units located in the vicinity of potential bomb damage to high-value structures or areas, or in the vicinity of potential bomb damage to other potential targets for bombs, each of said units providing for the transmission of a suppressant material therethrough, said transmission of suppressant material occurring prior to the explosion of the bomb whose blast effects are to be suppressed, each of said units having nozzles configured to disperse said suppressant material into the air where blast effects are to be suppressed, said suppressant material being dispersed at a given point in time having a weight, and the bomb has associated therewith an explosive having a weight, with the ratio of the weight of the suppressant material to the weight of explosive being in the range of between 0.2 and 4,
    a source of said suppressant material, and
    transmission lines connecting said source to said units.

29. A blast effects suppression system comprising
    a plurality of command-actuated units located in the vicinity of potential bomb damage to high-value structures or in the vicinity of potential bomb damage to other potential targets for bombs, each of said units providing for the transmission of a suppressant material therethrough, each of said units having nozzles configured to disperse said suppressant material into the air where blast effects are to be suppressed, a source of said suppressant material, transmission lines connecting said source to said units, and a sump.

30. A method of suppressing blast effects associated with a suspected bomb located in or adjacent to a building, so that the bomb blast will not damage the building, the method comprising the steps of having the suspected bomb surrounded by a plurality of command-actuated units, each of said units providing for the transmission of a suppressant material therethrough, and dispersing said suppressant material into the air surrounding the suspected bomb with said suppressant material continuing to be dispersed for a time after the explosion.

31. A method of suppressing blast effects associated with a suspected bomb located in or adjacent to a building, so that the bomb blast will not damage the building, the method comprising the steps of having the suspected bomb surrounded by a plurality of command-actuated units, each of said units providing for the transmission of a suppressant material therethrough, adjusting the droplet size of said suppressant material, and dispersing said suppressant material into the air surrounding the suspected bomb.

32. A method of suppressing blast effects associated with a suspected bomb, comprising the steps of having the suspected bomb surrounded by a plurality of command-actuated units, each of said units providing for the transmission of a suppressant material therethrough, dispersing said suppressant material into the air surrounding the suspected bomb, said suppressant material being dispersed at a given point in time having a weight, and the suspected bomb has associated therewith an explosive having a weight, with the ratio of the weight of the suppressant material to the weight of explosive being in the range of between 0.2 and 15.

* * * * *

UNITED STATES PATENT AND TRADEMARK OFFICE
CERTIFICATE OF CORRECTION

Figure 12:
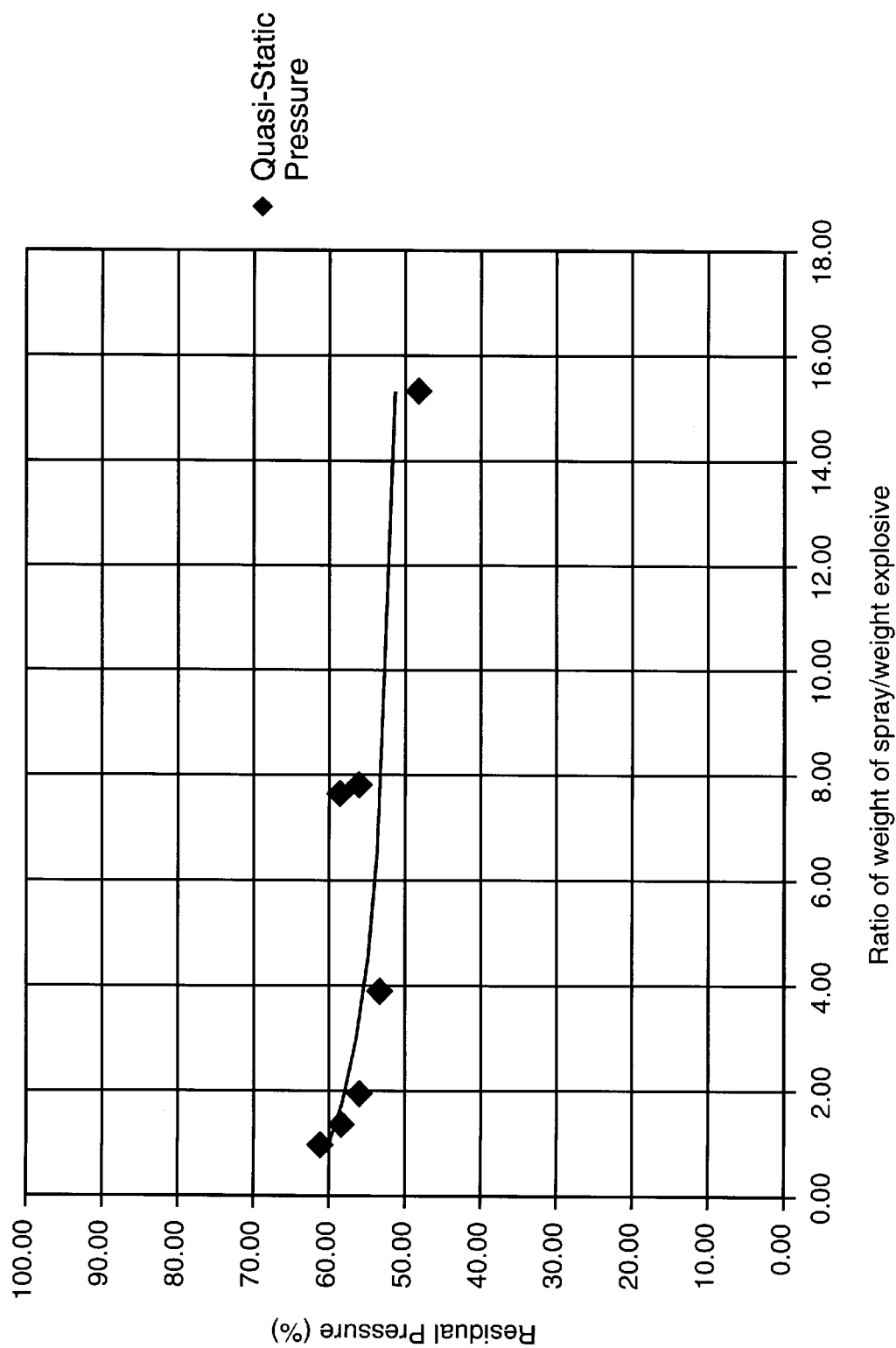
FIG. 12 discloses a graph demonstrating the reduction in quasi-static pressure associated with an explosion inside an enclosure when the system of this invention is in use.
Figure 13:
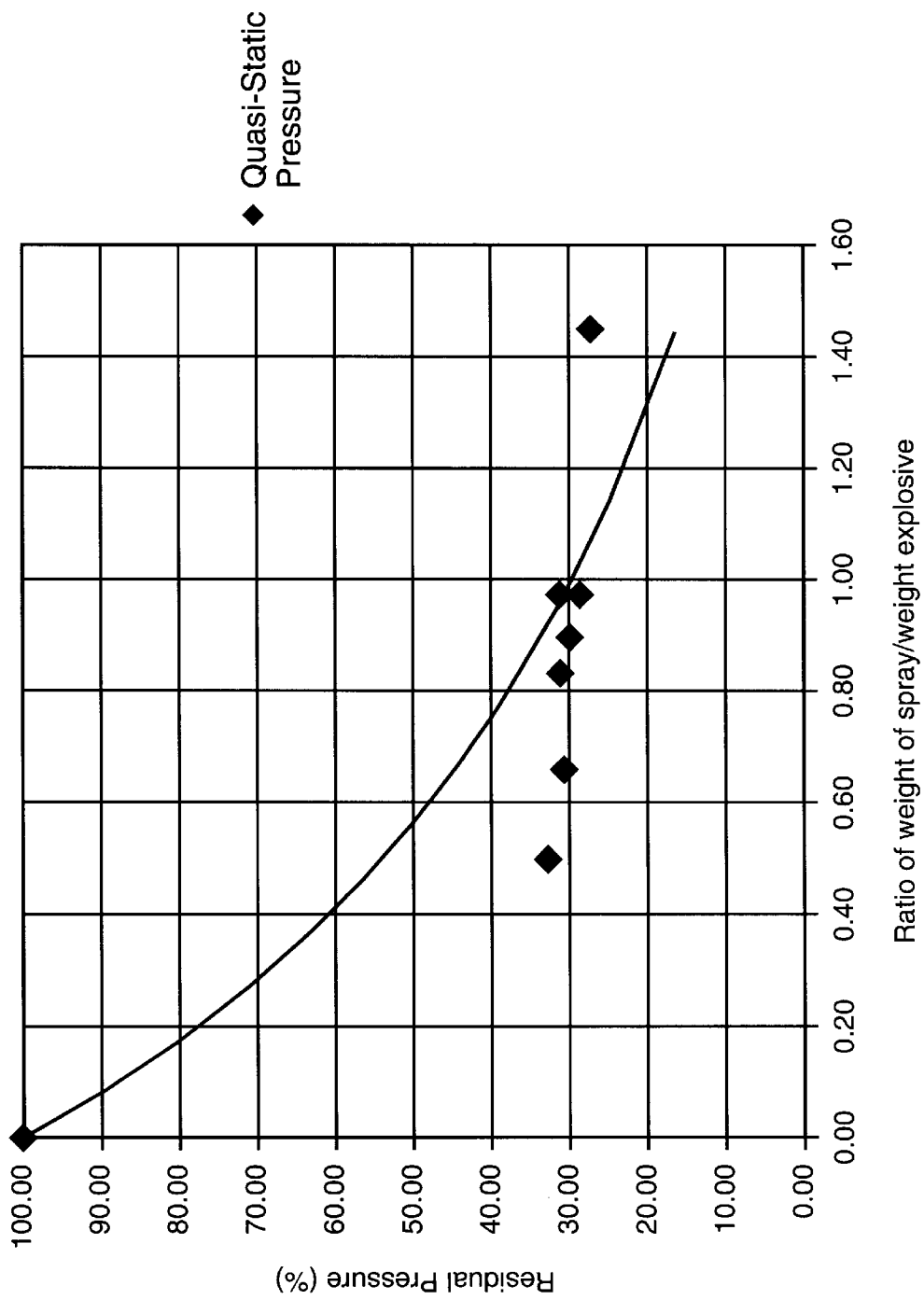
FIG. 13 discloses a graph demonstrating the reduction in quasi-static pressure associated with an explosion inside an enclosure when the system of this invention is in use, but with suppressant being applied from basically one side.

PATENT NO. : 6,119,574
DATED : September 19, 2000
INVENTOR(S) : Thomas E. Burky, Donald J. Butz, John S. Butz,
Scott M. Golly, and Graham H. Alexander It is certified that error appears in the above-identified patent and that said Letters Patent is hereby corrected as shown below:

Page 9, Figure 12, "Reduction of QuasiReduction of Quasi-Static Pressure" should be -- Reduction of Quasi-Static Pressure --.

Signed and Sealed this

First Day of May, 2001

*Attest:*

NICHOLAS P. GODICI

*Attesting Officer*   *Acting Director of the United States Patent and Trademark Office*